(12) United States Patent
Nettekoven et al.

(10) Patent No.: US 8,507,535 B2
(45) Date of Patent: *Aug. 13, 2013

(54) METHYL-PYRROLIDINE ETHER DERIVATIVES

(75) Inventors: Matthias Nettekoven, Grenzach-Wyhlen (DE); Hasane Ratni, Habsheim (FR); Walter Vifian, Gelterkinden (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/171,507

(22) Filed: Jun. 29, 2011

(65) Prior Publication Data

US 2012/0010212 A1    Jan. 12, 2012

(30) Foreign Application Priority Data

Jul. 7, 2010    (EP) ..................... 10168688

(51) Int. Cl.
*A61K 31/4439* (2006.01)
*C07D 401/14* (2006.01)

(52) U.S. Cl.
USPC ............... 514/343; 546/268.1; 546/279.1; 514/336; 514/340

(58) Field of Classification Search
USPC ............ 546/268.1, 276.4, 279.1; 514/336, 514/340, 343
See application file for complete search history.

(56) References Cited

U.S. PATENT DOCUMENTS 7,812,021 B2 * 10/2010 Jablonski et al. .......... 514/235.5
8,012,998 B2 * 9/2011 Jablonski et al. ............ 514/333
8,063,075 B2 * 11/2011 Jablonski et al. ............ 514/340

FOREIGN PATENT DOCUMENTS

WO    2009/019163    2/2009
WO    2009/024502    2/2009
WO    2009/150110    12/2009

OTHER PUBLICATIONS

Jablonski et al (2009): STN International HCAPLUS database, Columbus (OH), accession No. 2009: 1541033.*
Kamali, F., "Current Opinion in Investigational Drugs" 2(7):950-956 (2001).
Tooney et al., "Neuroscience Letters" 283:185-188 ( 2000).
PCT International Search Report Mailed Sep. 13, 2011—PCT/EP2011/061168.
Jung et al., "Neuroscience" 74:403-414 ( 1996).
Giardina et al., "Expert Opinion on Therapeutic Patents" 10:939-960 ( 2000).

* cited by examiner

*Primary Examiner* — Golam M M Shameem

(57) ABSTRACT

The invention relates to a compound of formula

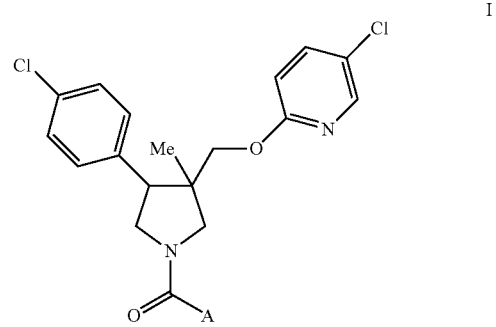

I wherein A is defined herein or to pharmaceutically active salts, stereoisomeric forms, including individual diastereoisomers and enantiomers of the compound of formula I as well as racemic and non-racemic mixtures thereof. The present compounds are high potential NK-3 receptor antagonists for the treatment of depression, pain, psychosis, Parkinson's disease, schizophrenia, anxiety and attention deficit hyperactivity disorder (ADHD).

10 Claims, No Drawings

METHYL-PYRROLIDINE ETHER DERIVATIVES

PRIORITY TO RELATED APPLICATION(S)

This application claims the benefit of European Patent Application No. 10168688.9, filed Jul. 7, 2010, which is hereby incorporated by reference in its entirety.

BACKGROUND OF THE INVENTION

The three main mammalian tachykinins, substance P (SP), neurokinin A (NKA) and neurokinin B (NKB) belong to the family of neuropeptides sharing the common COOH-terminal pentapeptide sequence of Phe-X-Gly-Leu-Met-$NH_2$. As neurotransmitters, these peptides exert their biological activity via three distinct neurokinin (NK) receptors termed as NK-1, NK-2 and NK-3. SP binds preferentially to the NK-1 receptor, NKA to the NK-2 and NKB to the NK-3 receptor.

The NK-3 receptor is characterized by a predominant expression in CNS and its involvement in the modulation of the central monoaminergic system has been shown. These properties make the NK-3 receptor a potential target for central nervous system disorders such as anxiety, depression, bipolar disorders, Parkinson's disease, schizophrenia and pain (*Neurosci. Letters,* 2000, 283, 185-188; *Exp. Opin. Ther. Patents* 2000, 10, 939-960; *Neuroscience,* 1996, 74, 403-414; *Neuropeptides,* 1998, 32, 481-488).

Schizophrenia is one of the major neuropsychiatric disorders, characterized by severe and chronic mental impairment. This devastating disease affects about 1% of the world's population. Symptoms begin in early adulthood and are followed by a period of interpersonal and social dysfunction. Schizophrenia manifests as auditory and visual hallucinations, paranoia, delusions (positive symptoms), blunted affect, depression, anhedonia, poverty of speech, memory and attention deficits as well as social withdrawal (negative symptoms).

For decades scientists and clinicians have made efforts with the aim of discovering an ideal agent for the pharmacological treatment of schizophrenia. However, the complexity of the disorders, due to a wide array of symptoms, has hampered those efforts. There are no specific focal characteristics for the diagnosis of schizophrenia and no single symptom is consistently present in all patients. Consequently, the diagnosis of schizophrenia as a single disorder or as a variety of different disorders has been discussed but not yet resolved. The major difficulty in the development of a new drug for schizophrenia is the lack of knowledge about the cause and nature of this disease. Some neurochemical hypotheses have been proposed on the basis of pharmacological studies to rationalize the development of a corresponding therapy: the dopamine, the serotonin and the glutamate hypotheses. But taking into account the complexity of schizophrenia, an appropriate multireceptor affinity profile might be required for efficacy against positive and negative signs and symptoms. Furthermore, an ideal drug against schizophrenia would preferably have a low dosage allowing once-per-day dosage, due to the low adherence of schizophrenic patients.

In recent years clinical studies with selective NK1 and NK2 receptor antagonists appeared in the literature showing results for the treatment of emesis, depression, anxiety, pain and migraine (NK1) and asthma (NK2 and NK1). The most exciting data were produced in the treatment of chemotherapy-induced emesis, nausea and depression with NK1 and in asthma with NK2-receptor antagonists. In contrast, no clinical data on NK3 receptor antagonists have appeared in the literature until 2000. Osanetant (SR 142,801) from Sanofi-Synthelabo was the first identified potent and selective non-peptide antagonist described for the NK3 tachykinin receptor for the potential treatment of schizophrenia, which was reported in the literature (*Current Opinion in Investigational Drugs,* 2001, 2(7), 950-956 and *Psychiatric Disorders Study* 4, *Schizophrenia,* June 2003, Decision Resources, Inc., Waltham, Mass.). The proposed drug SR 142,801 has been shown in a phase II trial as active on positive symptoms of schizophrenia, such as altered behaviour, delusion, hallucinations, extreme emotions, excited motor activity and incoherent speech, but inactive in the treatment of negative symptoms, which are depression, anhedonia, social isolation or memory and attention deficits.

The neurokinin-3 receptor antagonists have been described as useful in pain or inflammation, as well as in schizophrenia, *Exp. Opinion. Ther. Patents* (2000), 10(6), 939-960 and *Current Opinion in Investigational Drugs,* 2001, 2(7), 950-956 956 and *Psychiatric Disorders Study* 4, *Schizophrenia,* June 2003, Decision Resources, Inc., Waltham, Mass.).

SUMMARY OF THE INVENTION

The invention provides a compound of formula

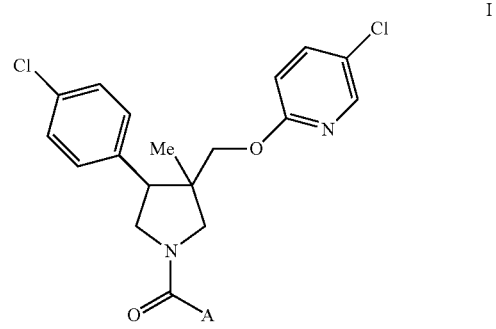

wherein
A is selected from the groups (a), (b) or (c):

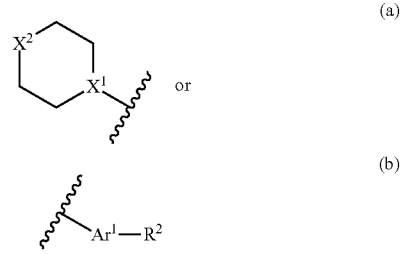

or is cycloalkyl, optionally substituted by lower alkyl (c);
$Ar^1$ is phenyl or a six membered heteroaryl;
$X^1$ is N or CH;
$X^2$ is N—$R^1$ or O;
$R^1$ is $S(O)_2$-lower alkyl, C(O)-cycloalkyl substituted by lower alkyl, or is C(O)-lower alkyl, lower alkyl, cyano, cycloalkyl or is a six membered heteroaryl substituted by lower alkyl, cyano, C(O)-lower alkyl, halogen, lower alkyl substituted by halogen or lower alkoxy; or is phenyl substituted by cyano or halogen;
$R^2$ is lower alkyl, halogen, pyrazolyl, 3-methyl-[1,2,4]oxazolyl, 5-methyl-[1,2,4]oxadiazol-3-yl, pyridyl substituted by cyano, or is phenyl substituted by halogen, or is cyano, lower alkoxy, or is piperidin-2-one;
or to pharmaceutically active salts, stereoisomeric forms, including individual diastereoisomers and enantiomers of the compound of formula I as well as racemic and non-racemic mixtures thereof.

The invention provides novel compounds of formula I per se, pharmaceutically acceptable salts of such compounds, and pharmaceutical compositions containing them. The invention also provides methods for the manufacture of such compounds and compositions. The invention further provides methods for the control or prevention of illnesses such as depression, pain, bipolar disorders, psychosis, Parkinson's disease, schizophrenia, anxiety and attention deficit hyperactivity disorder (ADHD) which comprise administering compounds or compositions of the invention.

The present compounds are high potential NK-3 receptor antagonists for the treatment of depression, pain, psychosis, Parkinson's disease, schizophrenia, anxiety and attention deficit hyperactivity disorder (ADHD).

The preferred indications using the compounds of the present invention are depression, psychosis, Parkinson's disease, schizophrenia, anxiety and attention deficit hyperactivity disorder (ADHD).

DETAILED DESCRIPTION OF THE INVENTION

The following definitions of the general terms used in the present description apply irrespective of whether the terms in question appear alone or in combination.

As used herein, the term "lower alkyl" denotes a straight- or branched-hydrocarbon chain group containing from 1-8 carbon atoms, for example, methyl, ethyl, propyl, isopropyl, n-butyl, i-butyl, t-butyl and the like. Preferred lower alkyl groups are groups with 1-4 carbon atoms.

The term "lower alkyl substituted by halogen" denotes an alkyl group as defined above, wherein at least one hydrogen atom is replaced by halogen, for example —$CF_3$, —$CHF_2$, —$CH_2F$, —$CH_2CF_3$, —$CH_2CH_2CF_3$, —$CH_2CF_2CF_3$ and the like. Preferred lower alkyl substituted by halogen groups are groups having 1-4 carbon atoms.

The term "halogen" denotes chlorine, iodine, fluorine and bromine.

The term "lower alkoxy" denotes a group of the formula —O—R', wherein R' is a lower alkyl group as defined above. Examples of alkoxy moieties include methoxy, ethoxy, isopropoxy, and tert-butoxy.

The term "cycloalkyl" denotes a monovalent saturated monocyclic or bicyclic hydrocarbon group of 3 to 10 ring carbon atoms, particularly a monovalent saturated monocyclic hydrocarbon group of 3 to 8 ring carbon atoms. Bicyclic means consisting of two saturated carbocycles having one or more carbon atoms in common. Particular cycloalkyl groups are monocyclic. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl, or bicyclo[2.2.2]octanyl.

The term "six membered heteroaryl" denotes a cyclic aromatic hydrocarbon radical which contains at least one N-heteroatom, for example pyridinyl or pyridazinyl.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

The terms "therapeutically inert carrier" and "pharmaceutically acceptable excipient" denote any ingredient having no therapeutic activity and being non-toxic such as disintegrators, binders, fillers, solvents, buffers, tonicity agents, stabilizers, antioxidants, surfactants or lubricants used in formulating pharmaceutical products.

The term "therapeutically effective amount" denotes an amount of a compound of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, disease state being treated, the severity or the disease treated, the age and relative health of the subject, the route and form of administration, the judgement of the attending medical or veterinary practitioner, and other factors.

One embodiment of the invention provides compounds of formula IA for A being

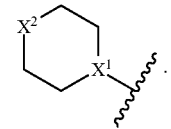

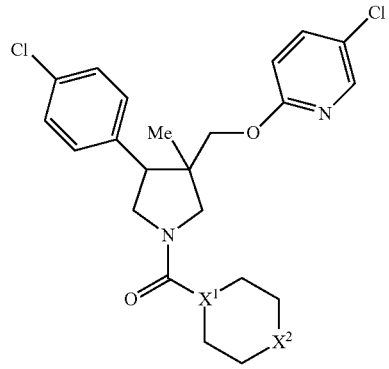

IA $X^1$ is N or CH;
$X^2$ is N—$R^1$ or O;
$R^1$ is $S(O)_2$-lower alkyl, C(O)-cycloalkyl substituted by lower alkyl, or is C(O)-lower alkyl, lower alkyl, cyano, cycloalkyl or is a six membered heteroaryl substituted by lower alkyl, cyano, C(O)-lower alkyl, halogen, lower alkyl substituted by halogen or lower alkoxy; or is phenyl substituted by cyano or halogen;
or pharmaceutically active salts, stereoisomeric forms, including individual diastereoisomers and enantiomers of the compound of formula I as well as racemic and non-racemic mixtures thereof, for example the following compounds:

[(3RS,4RS)-4-(4-chloro-phenyl)-3-(5-chloro-pyridin-2-yloxymethyl)-3-methyl-pyrrolidin-1-yl]-(4-methane sulfonyl-piperazin-1-yl)-methanone;

[(3RS,4RS)-4-(4-chloro-phenyl)-3-(5-chloro-pyridin-2-yloxymethyl)-3-methyl-pyrrolidin-1-yl]-[1-(1-methyl-cyclopropanecarbonyl)-piperidin-4-yl]-methanone;

[(3RS,4RS)-4-(4-chloro-phenyl)-3-(5-chloro-pyridin-2-yloxymethyl)-3-methyl-pyrrolidin-1-yl]-(tetrahydro-pyran-4-yl)-methanone;

1-{4-[(3RS,4RS)-4-(4-chloro-phenyl)-3-(5-chloro-pyridin-2-yloxymethyl)-3-methyl-pyrrolidine-1-carbonyl]-piperidin-1-yl}-ethanone;

[(3RS,4RS)-4-(4-chloro-phenyl)-3-(5-chloro-pyridin-2-yloxymethyl)-3-methyl-pyrrolidin-1-yl]-(1-isobutyl-piperidin-4-yl)-methanone;

1-{4-[(3RS,4RS)-4-(4-chloro-phenyl)-3-(5-chloro-pyridin-2-yloxymethyl)-3-methyl-pyrrolidine-1-carbonyl]-piperidin-1-yl}-2-methyl-propan-1-one;

[(3RS,4RS)-4-(4-chloro-phenyl)-3-(5-chloro-pyridin-2-yloxymethyl)-3-methyl-pyrrolidin-1-yl]-(1-cyclohexyl-piperidin-4-yl)-methanone;

[(3RS,4RS)-4-(4-chloro-phenyl)-3-(5-chloro-pyridin-2-yloxymethyl)-3-methyl-pyrrolidin-1-yl]-(5'-methyl-3,4,5,6-tetrahydro-2H-[1,2']bipyridinyl-4-yl)-methanone;

4-[(3RS,4RS)-4-(4-chloro-phenyl)-3-(5-chloro-pyridin-2-yloxymethyl)-3-methyl-pyrrolidine-1-carbonyl]-3,4,5,6-tetrahydro-2H-[1,2']bipyridinyl-5'-carbonitrile;

4-{4-[(3RS,4RS)-4-(4-chloro-phenyl)-3-(5-chloro-pyridin-2-yloxymethyl)-3-methyl-pyrrolidine-1-carbonyl]-piperidin-1-yl}-benzonitrile;

1-{4-[(3RS,4RS)-4-(4-chloro-phenyl)-3-(5-chloro-pyridin-2-yloxymethyl)-3-methyl-pyrrolidine-1-carbonyl]-3,4,5,6-tetrahydro-2H-[1,2']bipyridinyl-5'-yl}-ethanone;

[(3RS,4RS)-4-(4-chloro-phenyl)-3-(5-chloro-pyridin-2-yloxymethyl)-3-methyl-pyrrolidin-1-yl]-(5'-fluoro-3,4,5,6-tetrahydro-2H-[1,2']bipyridinyl-4-yl)-methanone;

[(3RS,4RS)-4-(4-chloro-phenyl)-3-(5-chloro-pyridin-2-yloxymethyl)-3-methyl-pyrrolidin-1-yl]-(5'-chloro-3,4,5,6-tetrahydro-2H-[1,2']bipyridinyl-4-yl)-methanone;

[(3RS,4RS)-4-(4-chloro-phenyl)-3-(5-chloro-pyridin-2-yloxymethyl)-3-methyl-pyrrolidin-1-yl]-(5'-trifluoromethyl-3,4,5,6-tetrahydro-2H-[1,2']bipyridinyl-4-yl)-methanone;

4-[(3RS,4RS)-4-(4-chloro-phenyl)-3-(5-chloro-pyridin-2-yloxymethyl)-3-methyl-pyrrolidine-1-carbonyl]-3,4,5,6-tetrahydro-2H-[1,3']bipyridinyl-6'-carbonitrile; and

[(3R,4R)-4-(4-chloro-phenyl)-3-(5-chloro-pyridin-2-yloxymethyl)-3-methyl-pyrrolidin-1-yl]-[1-(6-methoxy-pyridazin-3-yl)-piperidin-4-yl]-methanone.

A further embodiment of the invention provides compounds of formula IB for A being

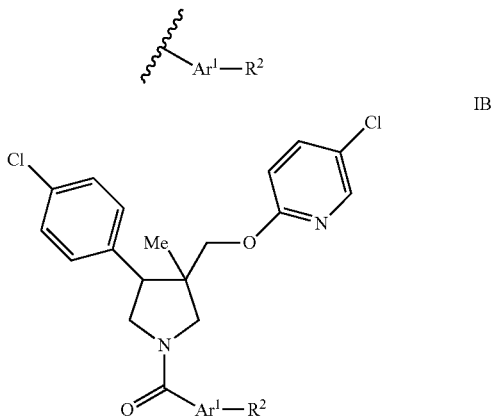

IB

Ar¹ is phenyl or a six membered heteroaryl;
R² is lower alkyl, halogen, pyrazolyl, 3-methyl-[1,2,4]oxazolyl, 5-methyl-[1,2,4]oxadiazol-3-yl, pyridyl substituted by cyano, or is phenyl substituted by halogen, or is cyano, lower alkoxy, or is piperidin-2-one;
or pharmaceutically active salts, stereoisomeric forms, including individual diastereoisomers and enantiomers of the compound of formula I as well as racemic and non-racemic mixtures thereof, for example the following compounds:

[(3RS,4RS)-4-(4-chloro-phenyl)-3-(5-chloro-pyridin-2-yloxymethyl)-3-methyl-pyrrolidin-1-yl]-(6-methyl-pyridazin-4-yl)-methanone;

[(3RS,4RS)-4-(4-chloro-phenyl)-3-(5-chloro-pyridin-2-yloxymethyl)-3-methyl-pyrrolidin-1-yl]-(1-methyl-cyclopropyl)-methanone;

[(3RS,4RS)-4-(4-chloro-phenyl)-3-(5-chloro-pyridin-2-yloxymethyl)-3-methyl-pyrrolidin-1-yl]-(6-pyrazol-1-yl-pyridin-3-yl)-methanone;

[(3RS,4RS)-4-(4-chloro-phenyl)-3-(5-chloro-pyridin-2-yloxymethyl)-3-methyl-pyrrolidin-1-yl]-[4-(3-methyl-[1,2,4]oxadiazol-5-yl)-phenyl]-methanone;

4-[(3RS,4RS)-4-(4-chloro-phenyl)-3-(5-chloro-pyridin-2-yloxymethyl)-3-methyl-pyrrolidine-1-carbonyl]-benzonitrile;

[(3RS,4RS)-4-(4-chloro-phenyl)-3-(5-chloro-pyridin-2-yloxymethyl)-3-methyl-pyrrolidin-1-yl]-(6-methoxy-pyridin-3-yl)-methanone;

5-[(3RS,4RS)-4-(4-chloro-phenyl)-3-(5-chloro-pyridin-2-yloxymethyl)-3-methyl-pyrrolidine-1-carbonyl]-pyridine-2-carbonitrile; [(3RS,4RS)-4-(4-chloro-phenyl)-3-(5-chloro-pyridin-2-yloxymethyl)-3-methyl-pyrrolidin-1-yl]-(4'-fluoro-biphenyl-4-yl)-methanone;

[(3RS,4RS)-4-(4-chloro-phenyl)-3-(5-chloro-pyridin-2-yloxymethyl)-3-methyl-pyrrolidin-1-yl]-[4-(5-methyl-[1,2,4]oxadiazol-3-yl)-phenyl]-methanone; and 1-{4-[(3RS,4RS)-4-(4-chloro-phenyl)-3-(5-chloro-pyridin-2-yloxymethyl)-3-methyl-pyrrolidine-1-carbonyl]-phenyl}-piperidin-2-one.

A further embodiment of the invention provides compounds of formula I for A being cycloalkyl, optionally substituted by lower alkyl (c).

The preparation of compounds of formula I of the present invention can be carried out in sequential or convergent synthetic routes. Syntheses of the compounds of the invention are shown in the following schemes. The skills required for carrying out the reaction and purification of the resulting products are known to those skilled in the art. The substituents and indices used in the following description of the processes have the significance given herein before unless indicated to the contrary.

The compounds of formula I can be manufactured by the methods given below, by the methods given in the examples or by analogous methods. Appropriate reaction conditions for the individual reaction steps are known to a person skilled in the art. The reaction sequence is not limited to the one displayed in scheme 1, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The present compounds of formula I and their pharmaceutically acceptable salts can be prepared by methods, known in the art, for example by the process described below, which process comprises a) coupling a compound of formula

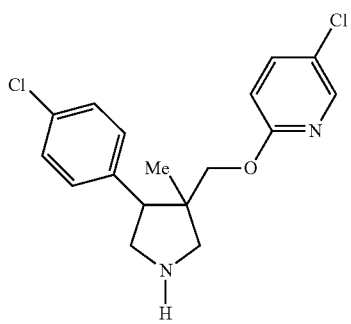

VII with a suitable acid chloride or carboxylic acid of formula

wherein L is halogen or hydroxy, to obtain a compound of formula

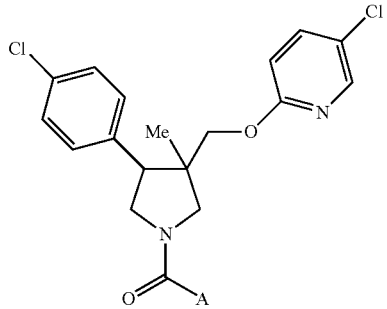

I wherein the group A is described above, and, if desired, converting the compounds of formula I into pharmaceutically acceptable acid addition salts.

Scheme 1

Preparation of derivatives of formula I

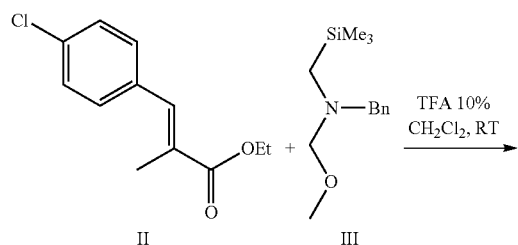

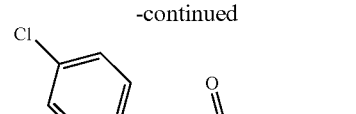

IV

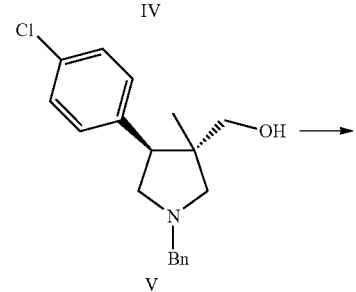

V

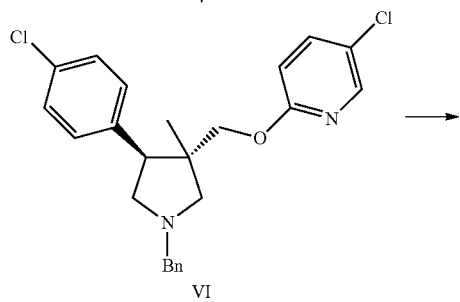

VI

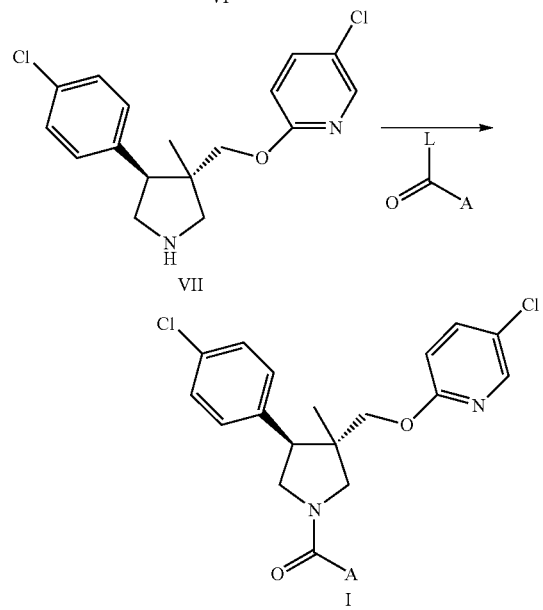

The 3,4-disubstituted pyrrolidines IV are prepared via a stereo specific 1,3-dipolar cycloaddition between the (E)-2-methyl-3-phenyl-acrylic acid ethyl ester derivatives II and the azomethine glide generated in situ from the N-(methoxymethyl)-N-(phenylmethyl)-N-(trimethylsilyl)methylamine III in the presence of a catalytic amount of acid, such as TFA. The phenyl substituted (E)-2-methyl-3-phenyl-acrylic acid ethyl ester derivatives II are either commercially available or prepared according to a general procedure described in literature (e.g. *J. Org. Chem.* 1966, 31(12), 4043-7). Reduction of the ester moiety using standard conditions for example LiAlH$_4$ yields the alcohol V. A Standard Mitsunobu reaction with for example a phenol, pyridin-ol or pyrimidin-ol give the aryl-ether VI. Alternatively a nucleophilic aromatic substitution reaction with a substituted 2-fluoro or 2-chloro pyridine derivatives give as well the aryl ether VI. Selective N-debenzylation is then carried out using several known procedures which are compatible with the substitution patterns of the aromatic rings to afford VII. A coupling with a suitable acid chloride, carboxylic acid or carbamoyl chloride using known methods give I.

ABBREVIATIONS

CH$_2$Cl$_2$=dichloromethane;
DMAP=dimethylaminopyridine;
HOBt=1-hydroxy-benzotriazol hydrate;
EDC=1-(3-dimethylaminopropyl)-3-ethylcarbodiimide hydrochloride;
Et$_3$N=triethylamine;
EtOAc=ethyl acetate;
H=hexane;
RT=room temperature;
PPh$_3$=triphenylphosphine;
DBAD=di-tert-butyl azodicarboxylate General Procedure I Amid Coupling (Pyrrolidine VII and Carboxylic Acid)

To a stirred solution of a carboxylic acid derivative (commercially available or known in the literature) (1 mmol) in 10 mL of CH$_2$Cl$_2$ was added (1.3 mmol) of EDC, (1.3 mmol) of HOBt and Et$_3$N (1.3 mmol). After one hour at RT, was added a pyrrolidine intermediate of formula (VII). The mixture was stirred at RT over night and then poured onto water and extracted with CH$_2$Cl$_2$. The combined organic phases were dried over Na$_2$SO$_4$ and concentrated under vacuo. Flash chromatography or preparative HPLC afforded the title compound.

General Procedure II

Coupling Between a Pyrrolidine of Formula VII, and an Acid Chloride or Carbamoyl Chloride A solution of the pyrrolidine (1 mmol) of formula (VII) in CH$_2$Cl$_2$ (10 mL) was treated with Et$_3$N (1.2 mmol) and an acid chloride or carbamoyl chloride (1.2 mmol) and stirred at RT overnight. The reaction mixture was then poured onto water and extracted with CH$_2$Cl$_2$. The combined organic phases were dried over Na$_2$SO$_4$ and concentrated under vacuo. Purification by preparative HPLC yielded the title compound.

Description of Pyrrolidine Intermediates of Formula VII

Pyrrolidine VII-1

5-Chloro-2-[(3RS,4RS)-4-(4-chloro-phenyl)-3-methyl-pyrrolidin-3-ylmethoxy]-pyridine

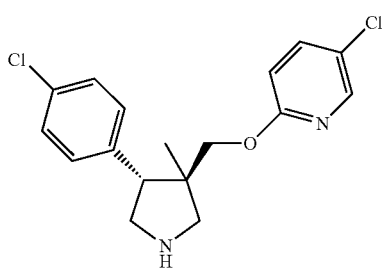 [SMILES: C[C@]1(COc2ccc(Cl)cn2)CNC[C@@H]1c1ccc(Cl)cc1]

a) (3RS,4RS)-1-Benzyl-4-(4-chloro-phenyl)-3-methyl-pyrrolidine-3-carboxylic acid ethyl ester A solution of N-(methoxymethyl)-N-(phenylmethyl)-N-(trimethylsilyl)methylamine (1.55 g, 6.54 mmol) in CH$_2$Cl$_2$ (5 mL) was added dropwise, over a 30 minutes period, to a stirred solution of (E)-3-(4-Chloro-phenyl)-2-methyl-acrylic acid ethyl ester (1.00 g, 4.45 mmol; preparation described in J. Org. Chem. 1966, 31: 4043-4047) and trifluoroacetic acid (0.034 mL, 0.44 mmol) in CH$_2$Cl$_2$ (10 mL) at 0° C. The ice bath was removed, and the solution was stirred at 25° C. for an additional 24 h. It was then concentrated and purification by flash chromatography (SiO$_2$, EtOAc/H 1:8) afforded 0.85 g (54%) of the title compound as a colorless oil. ES-MS m/e: 358.2 (M+H$^+$).

b) [(3RS,4RS)-1-Benzyl-4-(4-chloro-phenyl)-3-methyl-pyrrolidin-3-yl]-methanol

To a stirred solution of (3RS,4RS)-1-benzyl-4-(4-chloro-phenyl)-3-methyl-pyrrolidine-3-carboxylic acid ethyl ester (5.75 g, 16.7 mmol) in THF (200 mL) at 0° C., was added portion wise LiAlH$_4$ (381 mg, 10.0 mmol) over 20 minutes. After one hour at this temperature, the reaction mixture was carefully quenched by addition of icy water and then of an aqueous solution of NaHCO$_3$. The product was extracted with EtOAc several times, the combined organic phases were dried over NA$_2$SO$_4$ and purification by column chromatography (SiO$_2$, EtOAc/H 1:4 to 1:1) yielded the title product (4.0 g, 76%) as a colorless viscous oil. ES-MS m/e: 316.2 (M+H$^+$).

c) 2-[(3RS,4RS)-1-Benzyl-4-(4-chloro-phenyl)-3-methyl-pyrrolidin-3-ylmethoxy]-5-chloro-pyridine To a stirred solution of [(3RS,4RS)-1-benzyl-4-(4-chloro-phenyl)-3-methyl-pyrrolidin-3-yl]-methanol (4.0 g, 12.7 mmol) in DMF (60 mL) at RT was added NaH (608 mg, 60%, 15.2 mmol). The reaction mixture was heated at 50° C. for 30 minutes, then cooled down to RT before 2-bromo-5-chloro-pyridine (3.66 g, 19.0 mmol) was added. The resulting brownish solution was stirred overnight at 60° C., then concentrated under high vacuum. The residues was taken up in EtOAc, and washed with water. The organic phase was dried over Na$_2$SO$_4$ and a purification by column chromatography gave 3.90 g (72%) of the title product as a viscous oil. ES-MS m/e: 427.2 (M+H$^+$).

d) 5-Chloro-2-[(3RS,4RS)-4-(4-chloro-phenyl)-3-methyl-pyrrolidin-3-ylmethoxy]-pyridine To a stirred solution of 2-[(3RS,4RS)-1-benzyl-4-(4-chloro-phenyl)-3-methyl-pyrrolidin-3-ylmethoxy]-5-chloro-pyridine (0.70 g, 1.64 mmol) in toluene (10 mL) at RT was added 1-chloroethyl chloroformate (0.229 mL, 2.12 mmol) and iPr$_2$NEt (0.36 mL, 2.12 mmol). After 3 hours all volatiles were removed under high vacuum and the residue was dissolved in MeOH (10 mL). The reaction mixture was stirred at RT for 2 hours, and then concentrated under high vacuum. Column chromatography (SiO$_2$, CH$_2$Cl$_2$/MeOH, 9:1) afforded 595 mg (97%) of the title product as white foam. ES-MS m/e: 337.1 (M+H$^+$).

Example 1

[(3RS,4RS)-4-(4-Chloro-phenyl)-3-(5-chloro-pyridin-2-yloxymethyl)-3-methyl-pyrrolidin-1-yl]-(6-methyl-pyridazin-4-yl)-methanone

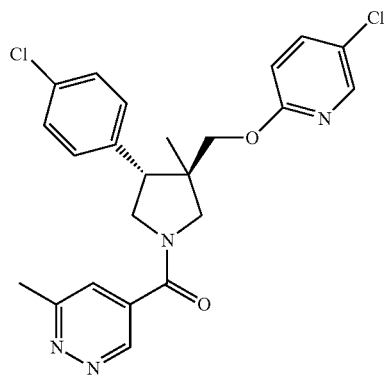 [SMILES: Cc1cc(C(=O)N2C[C@H](c3ccc(Cl)cc3)[C@@](C)(COc3ccc(Cl)cn3)C2)cnn1]

Amid coupling according to general procedure I:

Pyrrolidine intermediate: 5-Chloro-2-[(3RS,4RS)-4-(4-chloro-phenyl)-3-methyl-pyrrolidin-3-ylmethoxy]-pyridine (VII-1);

Carboxylic acid: 6-Methyl-pyridazine-4-carboxylic acid (preparation described in WO2009019163); ES-MS m/e: 457.2 (M+H$^+$).

Example 2

[(3RS,4RS)-4-(4-Chloro-phenyl)-3-(5-chloro-pyridin-2-yloxymethyl)-3-methyl-pyrrolidin-1-yl]-(4-methanesulfonyl-piperazin-1-yl)-methanone

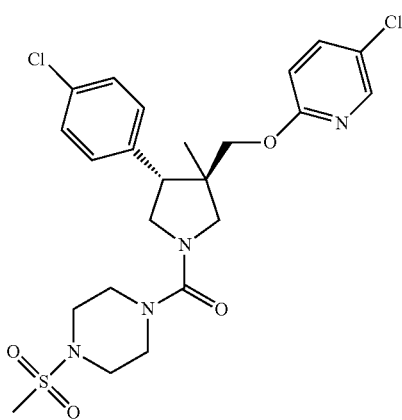 [SMILES: C[C@]1(COc2ccc(Cl)cn2)CN(C(=O)N2CCN(S(C)(=O)=O)CC2)C[C@@H]1c1ccc(Cl)cc1]

Coupling according to general procedure II:

Pyrrolidine intermediate: 5-Chloro-2-[(3RS,4RS)-4-(4-chloro-phenyl)-3-methyl-pyrrolidin-3-ylmethoxy]-pyridine (VII-1);

Carbamoyl chloride: 4-Methanesulfonyl-piperazine-1-carbonyl chloride (preparation described in WO2008128891);

ES-MS m/e: 527.3 (M+H$^+$).

Example 3

[(3RS,4RS)-4-(4-Chloro-phenyl)-3-(5-chloro-pyridin-2-yloxymethyl)-3-methyl-pyrrolidin-1-yl]-[1-(1-methyl-cyclopropanecarbonyl)-piperidin-4-yl]-methanone

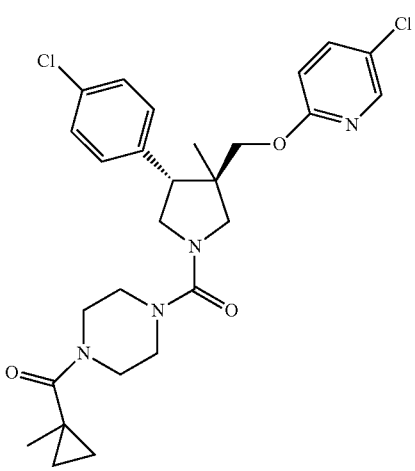 [SMILES: CC1(C(=O)N2CCN(C(=O)N3C[C@H](c4ccc(Cl)cc4)[C@@](C)(COc4ccc(Cl)cn4)C3)CC2)CC1]

Amid coupling according to general procedure I:

Pyrrolidine intermediate: 5-Chloro-2-[(3RS,4RS)-4-(4-chloro-phenyl)-3-methyl-pyrrolidin-3-ylmethoxy]-pyridine (VII-1);

Carboxylic acid: 1-(1-Methyl-cyclopropanecarbonyl)-piperidine-4-carboxylic acid (preparation described in US2009306043); ES-MS m/e: 530.1 (M+H$^+$).

Example 4

[(3RS,4RS)-4-(4-Chloro-phenyl)-3-(5-chloro-pyridin-2-yloxymethyl)-3-methyl-pyrrolidin-1-yl]-(1-methyl-cyclopropyl)-methanone

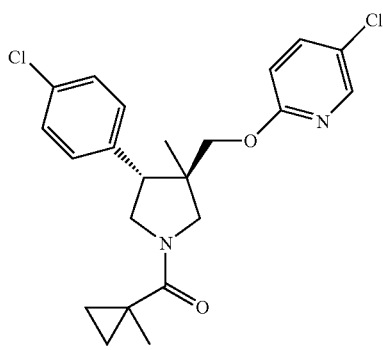 [SMILES: CC1(C(=O)N2C[C@H](c3ccc(Cl)cc3)[C@@](C)(COc3ccc(Cl)cn3)C2)CC1]

Amid coupling according to general procedure I:

Pyrrolidine intermediate: 5-Chloro-2-[(3RS,4RS)-4-(4-chloro-phenyl)-3-methyl-pyrrolidin-3-ylmethoxy]-pyridine (VII-1);

Carboxylic acid: 1-Methyl-cyclopropanecarboxylic acid (commercially available);

ES-MS m/e: 419.2 (M+H$^+$).

Example 5

[(3RS,4RS)-4-(4-Chloro-phenyl)-3-(5-chloro-pyridin-2-yloxymethyl)-3-methyl-pyrrolidin-1-yl]-(1-methyl-cyclopropyl)-methanone

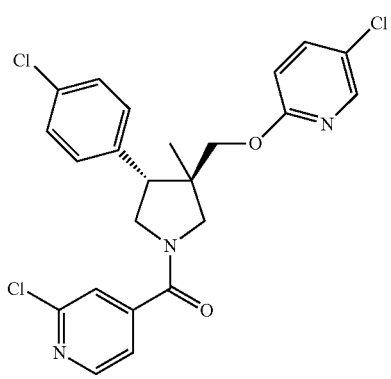 [SMILES: C[C@]1(COc2ccc(Cl)cn2)CN(C(=O)c2ccnc(Cl)c2)C[C@@H]1c1ccc(Cl)cc1]

Amid coupling according to general procedure I:

Pyrrolidine intermediate: 5-Chloro-2-[(3RS,4RS)-4-(4-chloro-phenyl)-3-methyl-pyrrolidin-3-ylmethoxy]-pyridine (VII-1);

Carboxylic acid: 2-Chloro-isonicotinic acid (commercially available); ES-MS m/e: 478.1 (M+H$^+$).

Example 6

[(3RS,4RS)-4-(4-Chloro-phenyl)-3-(5-chloro-pyridin-2-yloxymethyl)-3-methyl-pyrrolidin-1-yl]-(6-pyrazol-1-yl-pyridin-3-yl)-methanone

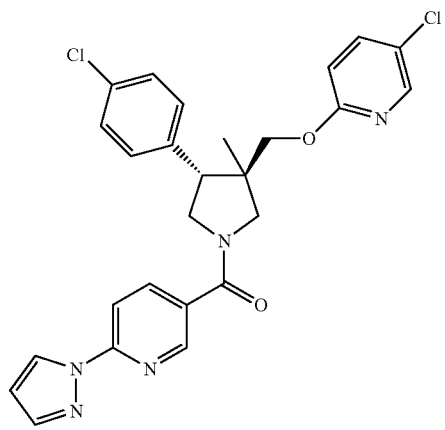 [SMILES: C[C@]1(COc2ccc(Cl)cn2)CN(C(=O)c2ccc(-n3cccn3)nc2)C[C@@H]1c1ccc(Cl)cc1]

Amid coupling according to general procedure I:

Pyrrolidine intermediate: 5-Chloro-2-[(3RS,4RS)-4-(4-chloro-phenyl)-3-methyl-pyrrolidin-3-ylmethoxy]-pyridine (VII-1);

Carboxylic acid: 6-Pyrazol-1-yl-nicotinic acid (commercially available); ES-MS m/e: 508.2 (M+H$^+$).

Example 7

[(3RS,4RS)-4-(4-Chloro-phenyl)-3-(5-chloro-pyridin-2-yloxymethyl)-3-methyl-pyrrolidin-1-yl]-[4-(3-methyl-[1,2,4]oxadiazol-5-yl)-phenyl]-methanone

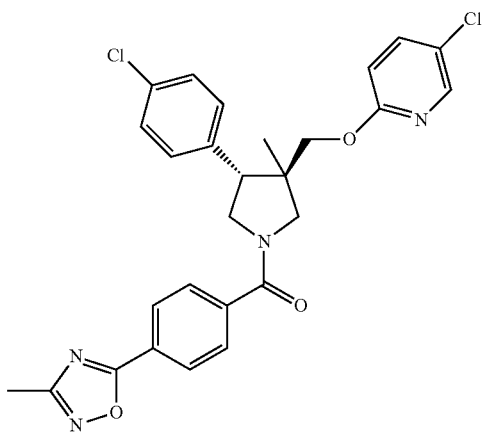 [SMILES: Cc1noc(-c2ccc(C(=O)N3C[C@H](c4ccc(Cl)cc4)[C@@](C)(COc4ccc(Cl)cn4)C3)cc2)n1]

Amid coupling according to general procedure I:

Pyrrolidine intermediate: 5-Chloro-2-[(3RS,4RS)-4-(4-chloro-phenyl)-3-methyl-pyrrolidin-3-ylmethoxy]-pyridine (VII-1);

Carboxylic acid: 4-(3-Methyl-[1,2,4]oxadiazol-5-yl)-benzoic acid (commercially available);

ES-MS m/e: 523.4 (M+H$^+$).

Example 8

4-[(3RS,4RS)-4-(4-Chloro-phenyl)-3-(5-chloro-pyridin-2-yloxymethyl)-3-methyl-pyrrolidine-1-carbonyl]-benzonitrile

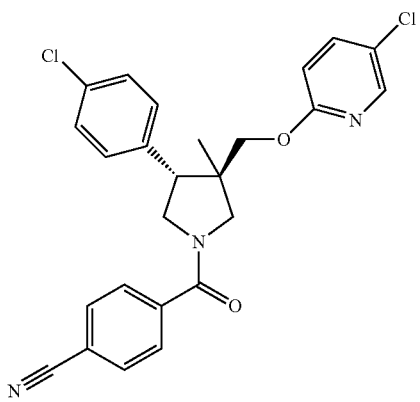 [SMILES: C[C@]1(COc2ccc(Cl)cn2)CN(C(=O)c2ccc(C#N)cc2)C[C@@H]1c1ccc(Cl)cc1]

Coupling according to general procedure II:

Pyrrolidine intermediate: 5-Chloro-2-[(3RS,4RS)-4-(4-chloro-phenyl)-3-methyl-pyrrolidin-3-ylmethoxy]-pyridine (VII-1);

Acid chloride: 4-Cyano-benzoyl chloride (commercially available);

ES-MS m/e: 466.2 (M+H$^+$).

Example 9

[(3RS,4RS)-4-(4-Chloro-phenyl)-3-(5-chloro-pyridin-2-yloxymethyl)-3-methyl-pyrrolidin-1-yl]-(6-methoxy-pyridin-3-yl)-methanone

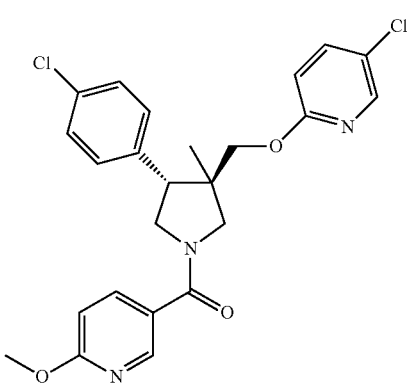 [SMILES: COc1ccc(C(=O)N2C[C@H](c3ccc(Cl)cc3)[C@@](C)(COc3ccc(Cl)cn3)C2)cn1]

Amid coupling according to general procedure I:

Pyrrolidine intermediate: 5-Chloro-2-[(3RS,4RS)-4-(4-chloro-phenyl)-3-methyl-pyrrolidin-3-ylmethoxy]-pyridine (VII-1);

Carboxylic acid: 6-Methoxy-nicotinic acid (commercially available);

ES-MS m/e: 472.3 (M+H$^+$).

Example 10

[(3RS,4RS)-4-(4-Chloro-phenyl)-3-(5-chloro-pyridin-2-yloxymethyl)-3-methyl-pyrrolidin-1-yl]-(tetrahydro-pyran-4-yl)-methanone

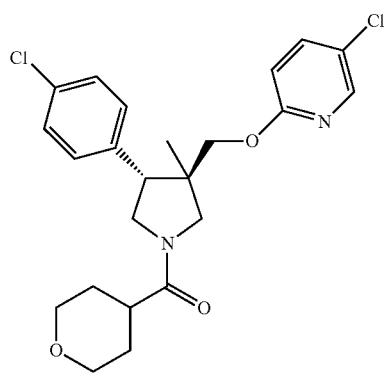 [SMILES: C[C@]1(COc2ccc(Cl)cn2)CN(C(=O)C2CCOCC2)C[C@@H]1c1ccc(Cl)cc1]

Coupling according to general procedure II:

Pyrrolidine intermediate: 5-Chloro-2-[(3RS,4RS)-4-(4-chloro-phenyl)-3-methyl-pyrrolidin-3-ylmethoxy]-pyridine (VII-1);

Acid chloride: Tetrahydro-pyran-4-carbonyl chloride (commercially available);

ES-MS m/e: 449.2 (M+H$^+$).

Example 11

1-{4-[(3RS,4RS)-4-(4-Chloro-phenyl)-3-(5-chloro-pyridin-2-yloxymethyl)-3-methyl-pyrrolidine-1-carbonyl]-piperidin-1-yl}-ethanone

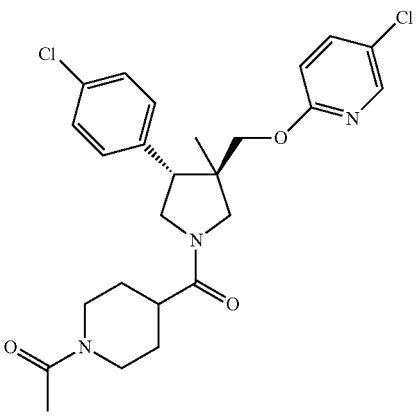 [SMILES: CC(=O)N1CCC(C(=O)N2C[C@H](c3ccc(Cl)cc3)[C@@](C)(COc3ccc(Cl)cn3)C2)CC1]

Amid coupling according to general procedure I:

Pyrrolidine intermediate: 5-Chloro-2-[(3RS,4RS)-4-(4-chloro-phenyl)-3-methyl-pyrrolidin-3-ylmethoxy]-pyridine (VII-1);

Carboxylic acid: 1-Acetyl-piperidine-4-carboxylic acid (commercially available);

ES-MS m/e: 490.2 (M+H$^+$).

Example 12

[(3RS,4RS)-4-(4-Chloro-phenyl)-3-(5-chloro-pyridin-2-yloxymethyl)-3-methyl-pyrrolidin-1-yl]-(1-isobutyl-piperidin-4-yl)-methanone

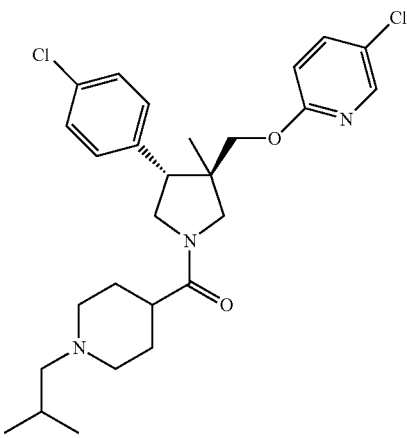 [SMILES: CC(C)CN1CCC(C(=O)N2C[C@H](c3ccc(Cl)cc3)[C@@](C)(COc3ccc(Cl)cn3)C2)CC1]

Amid coupling according to general procedure I:

Pyrrolidine intermediate: 5-Chloro-2-[(3RS,4RS)-4-(4-chloro-phenyl)-3-methyl-pyrrolidin-3-ylmethoxy]-pyridine (VII-1);

Carboxylic acid: 1-Isobutyl-piperidine-4-carboxylic acid (commercially available);

ES-MS m/e: 504.2 (M+H$^+$).

Example 13

1-{4-[(3RS,4RS)-4-(4-Chloro-phenyl)-3-(5-chloro-pyridin-2-yloxymethyl)-3-methyl-pyrrolidine-1-carbonyl]-piperidin-1-yl}-2-methyl-propan-1-one

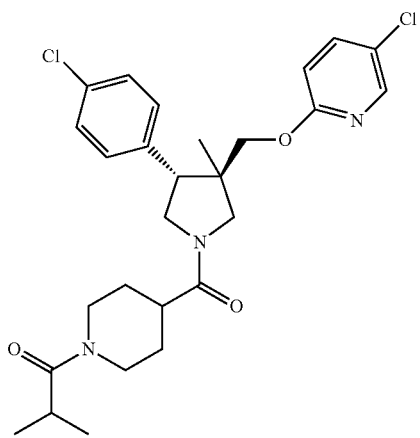 [SMILES: CC(C)C(=O)N1CCC(C(=O)N2C[C@H](c3ccc(Cl)cc3)[C@@](C)(COc3ccc(Cl)cn3)C2)CC1]

Amid coupling according to general procedure I:
Pyrrolidine intermediate: 5-Chloro-2-[(3RS,4RS)-4-(4-chloro-phenyl)-3-methyl-pyrrolidin-3-ylmethoxy]-pyridine (VII-1);
Carboxylic acid: 1-Isobutyryl-piperidine-4-carboxylic acid (commercially available);
ES-MS m/e: 518.5 (M+H$^+$).

Example 14

[(3RS,4RS)-4-(4-Chloro-phenyl)-3-(5-chloro-pyridin-2-yloxymethyl)-3-methyl-pyrrolidin-1-yl]-(1-cyclohexyl-piperidin-4-yl)-methanone

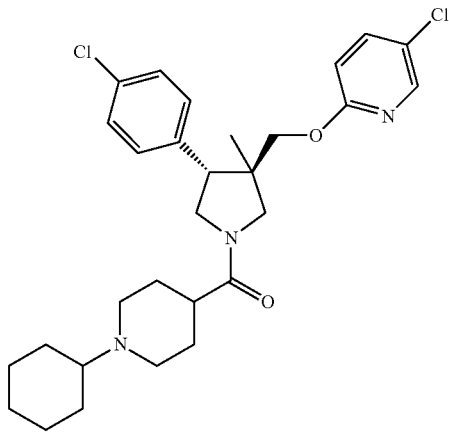 [SMILES: C[C@]1(COc2ccc(Cl)cn2)CN(C(=O)C2CCN(C3CCCCC3)CC2)C[C@@H]1c1ccc(Cl)cc1]

Amid coupling according to general procedure I:
Pyrrolidine intermediate: 5-Chloro-2-[(3RS,4RS)-4-(4-chloro-phenyl)-3-methyl-pyrrolidin-3-ylmethoxy]-pyridine (VII-1);
Carboxylic acid: 1-Cyclohexyl-piperidine-4-carboxylic acid (commercially available);
ES-MS m/e: 530.2 (M+H$^+$).

Example 15

[(3RS,4RS)-4-(4-Chloro-phenyl)-3-(5-chloro-pyridin-2-yloxymethyl)-3-methyl-pyrrolidin-1-yl]-(5'-methyl-3,4,5,6-tetrahydro-2H-[1,2']bipyridinyl-4-yl)-methanone

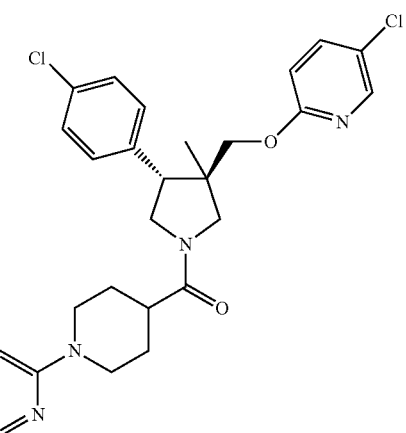

Amid coupling according to general procedure I:
Pyrrolidine intermediate: 5-Chloro-2-[(3RS,4RS)-4-(4-chloro-phenyl)-3-methyl-pyrrolidin-3-ylmethoxy]-pyridine (VII-1);
Carboxylic acid: 5'-Methyl-3,4,5,6-tetrahydro-2H-[1,2']bipyridinyl-4-carboxylic acid (commercially available);
ES-MS m/e: 539.4 (M+H$^+$).

Example 16

4-[(3RS,4RS)-4-(4-Chloro-phenyl)-3-(5-chloro-pyridin-2-yloxymethyl)-3-methyl-pyrrolidine-1-carbonyl]-3,4,5,6-tetrahydro-2H-[1,2']bipyridinyl-5'-carbonitrile

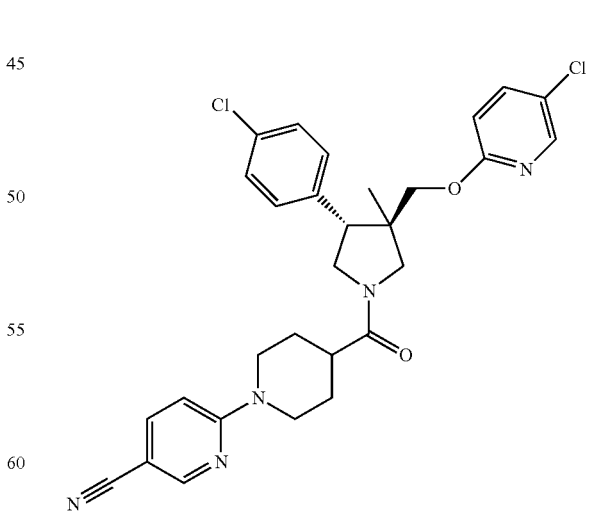

Amid coupling according to general procedure I:
Pyrrolidine intermediate: 5-Chloro-2-[(3RS,4RS)-4-(4-chloro-phenyl)-3-methyl-pyrrolidin-3-ylmethoxy]-pyridine (VII-1);

Carboxylic acid: 5'-Cyano-3,4,5,6-tetrahydro-2H-[1,2']bipyridinyl-4-carboxylic acid (commercially available); ES-MS m/e: 550.3 (M+H⁺).

Example 17

4-{4-[(3RS,4RS)-4-(4-Chloro-phenyl)-3-(5-chloro-pyridin-2-yloxymethyl)-3-methyl-pyrrolidine-1-carbonyl]-piperidin-1-yl}-benzonitrile

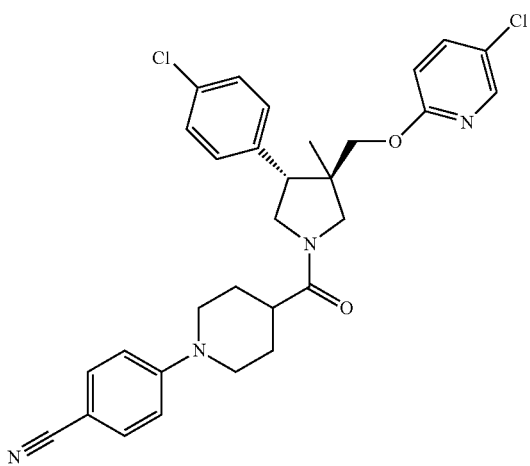 [SMILES: C[C@]1(COc2ccc(Cl)cn2)CN(C(=O)C2CCN(c3ccc(C#N)cc3)CC2)C[C@@H]1c1ccc(Cl)cc1]

Amid coupling according to general procedure I:
Pyrrolidine intermediate: 5-Chloro-2-[(3RS,4RS)-4-(4-chloro-phenyl)-3-methyl-pyrrolidin-3-ylmethoxy]-pyridine (VII-1);
Carboxylic acid: 1-(4-Cyano-phenyl)-piperidine-4-carboxylic acid (commercially available);
ES-MS m/e: 549.4 (MAI).

Example 18

1-{4-[(3RS,4RS)-4-(4-Chloro-phenyl)-3-(5-chloro-pyridin-2-yloxymethyl)-3-methyl-pyrrolidine-1-carbonyl]-3,4,5,6-tetrahydro-2H-[1,2']bipyridinyl-5'-yl}-ethanone

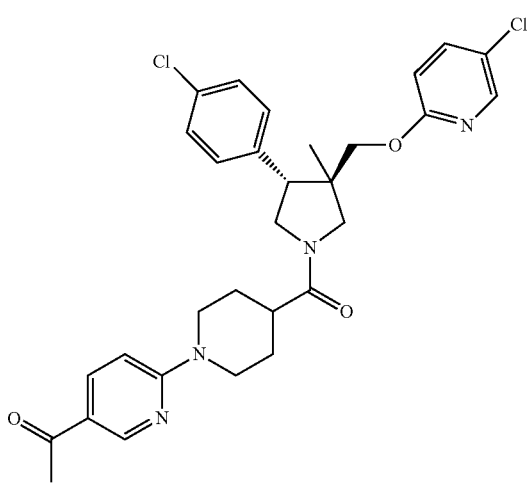 [SMILES: CC(=O)c1ccc(N2CCC(C(=O)N3C[C@H](c4ccc(Cl)cc4)[C@@](C)(COc4ccc(Cl)cn4)C3)CC2)nc1]

Amid coupling according to general procedure I:
Pyrrolidine intermediate: 5-Chloro-2-[(3RS,4RS)-4-(4-chloro-phenyl)-3-methyl-pyrrolidin-3-ylmethoxy]-pyridine (VII-1);
Carboxylic acid: 5'-Acetyl-3,4,5,6-tetrahydro-2H-[1,2']bipyridinyl-4-carboxylic acid (preparation described hereinafter); ES-MS m/e: 567.4 (M+H⁺).

Preparation of 5'-Acetyl-3,4,5,6-tetrahydro-2H-[1,2']bipyridinyl-4-carboxylic acid First Step:
To a stirred solution of piperidine-4-carboxylic acid ethyl ester (12.6 g, 0.080 mol) in CH₃CN (250 mol), iPr₂Net (33.7 mL, 0.193 mol) and 1-(6-chloro-pyridin-3-yl)-ethanone (10 g, 0.064 mol) were added. The reaction mixture was heated at reflux over night, and then volatiles evaporated under high vacuum. Column chromatography (SiO₂, EtOAc/heptane, 1:9 to 1:1) yielded 15.9 g (89%) of 5'-acetyl-3,4,5,6-tetrahydro-2H-[1,2']bipyridinyl-4-carboxylic acid ethyl ester as a yellow oil. ES-MS m/e: 277.2 (M+H⁺).

Second Step:
To a stirred solution of 5'-acetyl-3,4,5,6-tetrahydro-2H-[1,2']bipyridinyl-4-carboxylic acid ethyl ester (15.8 g, 0.057 mol) in THF (75 mL), H₂O (75 mL) and MeOH (8 mL) was added LiOH.H₂O (2.64 g, 0.0629 mol). Stirring was continued overnight at RT before the organic solvent were removed under vacuo. The pH of the was adjusted to 5 with acetic acid, and the white precipitate was filtered off and dried to yield 13 g (92%) of 5'-Acetyl-3,4,5,6-tetrahydro-2H-[1,2']bipyridinyl-4-carboxylic acid. ES-MS m/e: 249.2 (M–H⁺)

Example 19

[(3RS,4RS)-4-(4-Chloro-phenyl)-3-(5-chloro-pyridin-2-yloxymethyl)-3-methyl-pyrrolidin-1-yl]-(5'-fluoro-3,4,5,6-tetrahydro-2H-[1,2']bipyridinyl-4-yl)-methanone

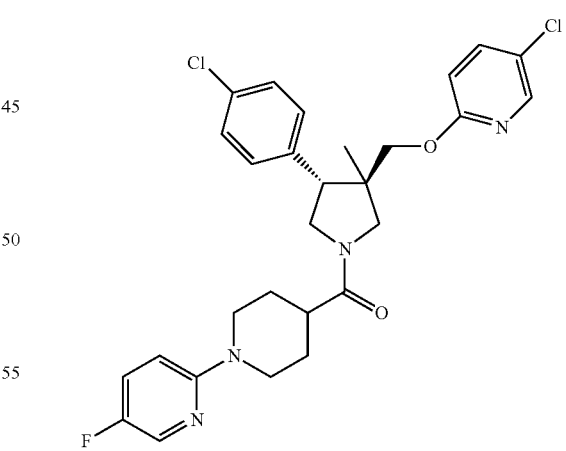

Amid coupling according to general procedure I:
Pyrrolidine intermediate: 5-Chloro-2-[(3RS,4RS)-4-(4-chloro-phenyl)-3-methyl-pyrrolidin-3-ylmethoxy]-pyridine (VII-1);
Carboxylic acid: 5'-Fluoro-3,4,5,6-tetrahydro-2H-[1,2']bipyridinyl-4-carboxylic acid (preparation described hereinafter);
ES-MS m/e: 543.3 (M+H⁺).

Preparation of 5'-Fluoro-3,4,5,6-tetrahydro-2H-[1,2] bipyridinyl-4-carboxylic acid First Step:

To a stirred solution of piperidine-4-carboxylic acid ethyl ester (14.3 g, 0.091 mol) and 2-chloro-5-fluoro-pyridine (10 g, 0.076 mol) in toluene (100 mol) was added NaOtBu (8.77 g, 0.091 mol), BINAP (1.42 g, 2.28 mmol) and tris(dibenilideneacetone)dipalladium(0) (1.39 g, 1.52 mmol). The reaction mixture was heated at 75° C. for 2 hours, cooled down to RT, and diluted with AcOEt (100 mL) and H$_2$O (100 mL). The organic layer was separated and washed with brine, dried over Na$_2$SO$_4$ and concentrated under vacuo. Column chromatography (SiO$_2$, EtOAc/heptane, 1:9 to 1:1) yielded 12.5 g (65%) of 5'-fluoro-3,4,5,6-tetrahydro-2H-[1,2']bipyridinyl-4-carboxylic acid ethyl ester as a yellow oil. ES-MS m/e: 253.3 (M+H$^+$).

Second Step:

To a stirred solution of 5'-fluoro-3,4,5,6-tetrahydro-2H-[1,2']bipyridinyl-4-carboxylic acid ethyl ester (12.5 g, 0.0495 mol) in THF (60 mL), H$_2$O (60 mL) and MeOH (6 mL) was added LiOH.H$_2$O (2.6 g, 0.0172 mol). Stirring was continued overnight at RT before the organic solvent were removed under vacuo. The pH of the was adjusted to 5 with acetic acid, and the white precipitate was filtered off and dried to yield 9.2 g (83%) of 5'-fluoro-3,4,5,6-tetrahydro-2H-[1,2']bipyridinyl-4-carboxylic acid. ES-MS m/e: 223.1 (M−H$^+$)

Example 20

[(3RS,4RS)-4-(4-Chloro-phenyl)-3-(5-chloro-pyridin-2-yloxymethyl)-3-methyl-pyrrolidin-1-yl]-(5'-chloro-3,4,5,6-tetrahydro-2H-[1,2']bipyridinyl-4-yl)-methanone

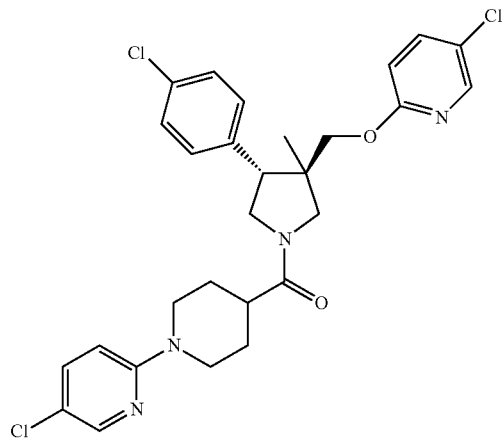 [SMILES: C[C@]1(COc2ccc(Cl)cn2)CN(C(=O)C2CCN(c3ccc(Cl)cn3)CC2)C[C@@H]1c1ccc(Cl)cc1]

Amid coupling according to general procedure I:
Pyrrolidine intermediate: 5-Chloro-2-[(3RS,4RS)-4-(4-chloro-phenyl)-3-methyl-pyrrolidin-3-ylmethoxy]-pyridine (VII-1);

Carboxylic acid: 5'-Chloro-3,4,5,6-tetrahydro-2H-[1,2']bipyridinyl-4-carboxylic acid (commercially available); ES-MS m/e: 561.0 (M+H$^+$).

Example 21

5-[(3RS,4RS)-4-(4-Chloro-phenyl)-3-(5-chloro-pyridin-2-yloxymethyl)-3-methyl-pyrrolidine-1-carbonyl]-pyridine-2-carbonitrile

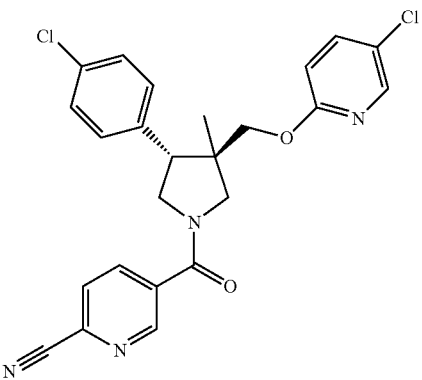 [SMILES: C[C@]1(COc2ccc(Cl)cn2)CN(C(=O)c2ccc(C#N)nc2)C[C@@H]1c1ccc(Cl)cc1]

Amid coupling according to general procedure I:
Pyrrolidine intermediate: 5-Chloro-2-[(3RS,4RS)-4-(4-chloro-phenyl)-3-methyl-pyrrolidin-3-ylmethoxy]-pyridine (VII-1);
Carboxylic acid: 6-Cyano-nicotinic acid (commercially available); ES-MS m/e: 467.2 (M+H$^+$).

Example 22

[(3RS,4RS)-4-(4-Chloro-phenyl)-3-(5-chloro-pyridin-2-yloxymethyl)-3-methyl-pyrrolidin-1-yl]-(5'-trifluoromethyl-3,4,5,6-tetrahydro-2H-[1,2']bipyridinyl-4-yl)-methanone

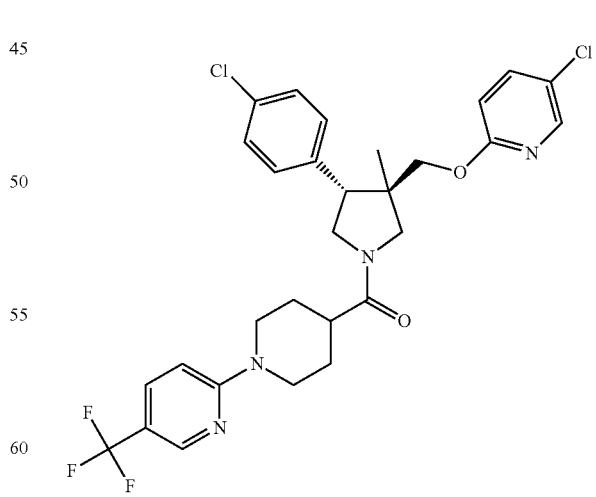

Amid coupling according to general procedure I:
Pyrrolidine intermediate: 5-Chloro-2-[(3RS,4RS)-4-(4-chloro-phenyl)-3-methyl-pyrrolidin-3-ylmethoxy]-pyridine (VII-1);

Carboxylic acid: 5'-Trifluoromethyl-3,4,5,6-tetrahydro-2H-[1,2']bipyridinyl-4-carboxylic acid (commercially available); ES-MS m/e: 593.4 (M+H⁺).

Example 23

[(3RS,4RS)-4-(4-Chloro-phenyl)-3-(5-chloro-pyridin-2-yloxymethyl)-3-methyl-pyrrolidin-1-yl]-(4'-fluoro-biphenyl-4-yl)-methanone

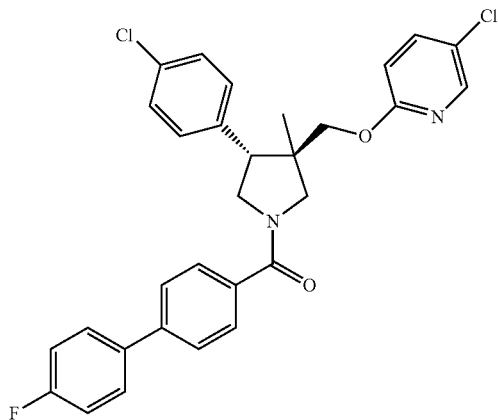 [SMILES: C[C@]1(COc2ccc(Cl)cn2)CN(C(=O)c2ccc(-c3ccc(F)cc3)cc2)C[C@@H]1c1ccc(Cl)cc1]

Amid coupling according to general procedure I:
Pyrrolidine intermediate: 5-Chloro-2-[(3RS,4RS)-4-(4-chloro-phenyl)-3-methyl-pyrrolidin-3-ylmethoxy]-pyridine (VII-1);
Carboxylic acid: 5'-Trifluoromethyl-3,4,5,6-tetrahydro-2H-[1,2']bipyridinyl-4-carboxylic acid (commercially available); ES-MS m/e: 535.2 (M+H⁺).

Example 24

[(3RS,4RS)-4-(4-Chloro-phenyl)-3-(5-chloro-pyridin-2-yloxymethyl)-3-methyl-pyrrolidin-1-yl]-[4-(5-methyl-[1,2,4]oxadiazol-3-yl)-phenyl]-methanone

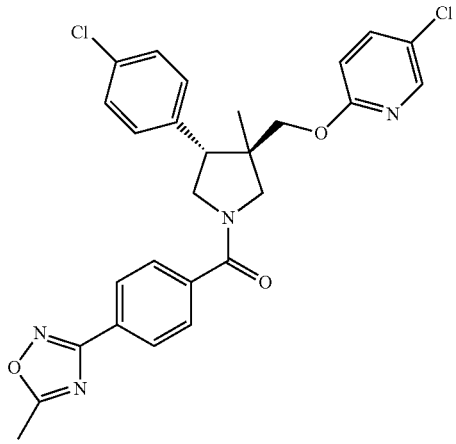 [SMILES: Cc1nc(-c2ccc(C(=O)N3C[C@H](c4ccc(Cl)cc4)[C@@](C)(COc4ccc(Cl)cn4)C3)cc2)no1]

Amid coupling according to general procedure I:
Pyrrolidine intermediate: 5-Chloro-2-[(3RS,4RS)-4-(4-chloro-phenyl)-3-methyl-pyrrolidin-3-ylmethoxy]-pyridine (VII-1);
Carboxylic acid: 4-(5-Methyl-[1,2,4]oxadiazol-3-yl)-benzoic acid (commercially available);
ES-MS m/e: 523.3 (M+H⁺).

Example 25

4-[(3RS,4RS)-4-(4-Chloro-phenyl)-3-(5-chloro-pyridin-2-yloxymethyl)-3-methyl-pyrrolidine-1-carbonyl]-3,4,5,6-tetrahydro-2H-[1,3']bipyridinyl-6'-carbonitrile Amid coupling according to general procedure I:
Pyrrolidine intermediate: 5-Chloro-2-[(3RS,4RS)-4-(4-chloro-phenyl)-3-methyl-pyrrolidin-3-ylmethoxy]-pyridine (VII-1);
Carboxylic acid: 6'-Cyano-3,4,5,6-tetrahydro-2H-[1,3]bipyridinyl-4-carboxylic acid (preparation described hereinafter); ES-MS m/e: 550.3 (M+H⁺).

Preparation of 6'-Cyano-3,4,5,6-tetrahydro-2H-[1,3]bipyridinyl-4-carboxylic acid First Step:

To a stirred solution of piperidine-4-carboxylic acid ethyl ester (3.70 g, 23.5 mmol) and 5-bromo-pyridine-2-carbonitrile (3.66 g, 20 mmol) in toluene (50 mol) was added NaOtBu (2.31 g, 24.0 mol), BINAP (374 mg, 0.60 mmol) and tris(dibenilideneacetone)dipalladium(0) (366 mg, 0.40 mmol). The reaction mixture was heated at 75° C. for 1 hours, cooled down to RT, and diluted with AcOEt (500 mL) and H₂O (50 mL). The organic layer was separated and washed with brine, dried over Na₂SO₄ and concentrated under vacuo. Column chromatography (SiO₂, EtOAc/heptane, 1:9 to 1:1) yielded 1.61 g (31%) of 6'-cyano-3,4,5,6-tetrahydro-2H-[1,3']bipyridinyl-4-carboxylic acid ethyl ester as a yellow oil. ES-MS m/e: 260.3 (M+H⁺)

Second Step:

To a stirred solution of 6'-cyano-3,4,5,6-tetrahydro-2H-[1,3]bipyridinyl-4-carboxylic acid ethyl ester (1.61 g, 6.20 mmol) in THF (30 mL), H₂O (30 mL) and MeOH (3 mL) was added LiOH.H₂O (326 mg, 7.76 mmol). Stirring was continued overnight at RT before the organic solvent were removed under vacuo. The pH of the was adjusted to 5 with acetic acid, and the product extracted with EtOAc, dried over Na₂SO₄.

The resulting solid was suspended in heptane, filtered off, washed with cold Et$_2$O to give 1.40 g (99%) of 6'-cyano-3,4,5,6-tetrahydro-2H-[1,3]bipyridinyl-4-carboxylic acid. ES-MS m/e: 230.1 (M–H$^+$)

Example 26

[(3R,4R)-4-(4-Chloro-phenyl)-3-(5-chloro-pyridin-2-yloxymethyl)-3-methyl-pyrrolidin-1-yl]-[1-(6-methoxy-pyridazin-3-yl)-piperidin-4-yl]-methanone

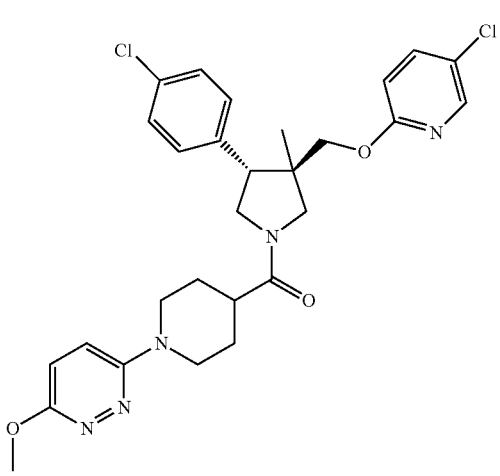 [SMILES: COc1ccc(N2CCC(C(=O)N3C[C@H](c4ccc(Cl)cc4)[C@@](C)(COc4ccc(Cl)cn4)C3)CC2)nn1]

Amid coupling according to general procedure I:

Pyrrolidine intermediate: 5-Chloro-2-[(3RS,4RS)-4-(4-chloro-phenyl)-3-methyl-pyrrolidin-3-ylmethoxy]-pyridine (VII-1);

Carboxylic acid: 1-(6-Methoxy-pyridazin-3-yl)-piperidine-4-carboxylic acid (preparation described hereinafter);

ES-MS m/e: 556.2 (M+H$^+$).

Preparation of 1-(6-Methoxy-pyridazin-3-yl)-piperidine-4-carboxylic acid

First Step:

To a stirred solution of piperidine-4-carboxylic acid ethyl ester (5.66 g, 36.0 mmol) and 3-chloro-6-methoxy-pyridazine (4.34 g, 30 mmol) in toluene (60 mol) was added NaOtBu (3.46 g, 36 mol), BINAP (560 mg, 0.90 mmol) and tris(dibenilideneacetone)dipalladium(0) (549 mg, 0.60 mmol). The reaction mixture was heated at 95° C. for 1 hours, cooled down to RT, and diluted with AcOEt (500 mL) and H$_2$O (50 mL). The organic layer was separated and washed with brine, dried over Na$_2$SO$_4$ and concentrated under vacuo. Column chromatography (SiO$_2$, EtOAc/heptane, 1:9 to 1:1) yielded 3.20 g (34%) of 1-(6-methoxy-pyridazin-3-yl)-piperidine-4-carboxylic acid ethyl ester as a yellow oil. ES-MS m/e: 266.3 (M+H$^+$).

Second Step:

To a stirred solution 1-(6-methoxy-pyridazin-3-yl)-piperidine-4-carboxylic acid ethyl ester (3.20 g, 12.06 mmol) in THF (40 mL), H$_2$O (40 mL) and MeOH (4 mL) was added LiOH.H$_2$O (600 mg, 14.3 mmol). Stirring was continued overnight at RT before the organic solvent were removed under vacuo. The pH of the was adjusted to 5 with acetic acid, and the product extracted with EtOAc, dried over Na$_2$SO$_4$.

The resulting solid was suspended in heptane, filtered off, washed with cold Et$_2$O to give 1.48 g (61%) of 1-(6-methoxy-pyridazin-3-yl)-piperidine-4-carboxylic acid. ES-MS m/e: 236.2 (M–H$^+$)

Example 27

1-{4-[(3RS,4RS)-4-(4-Chloro-phenyl)-3-(5-chloro-pyridin-2-yloxymethyl)-3-methyl-pyrrolidine-1-carbonyl]-phenyl}-piperidin-2-one

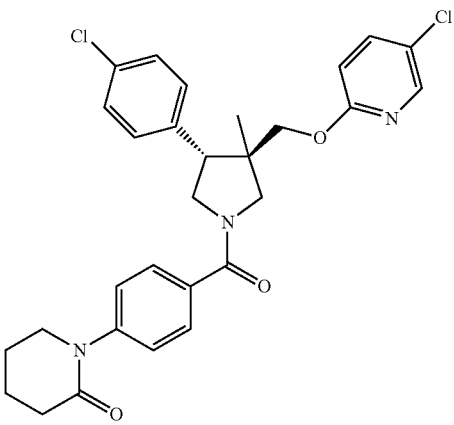 [SMILES: C[C@]1(COc2ccc(Cl)cn2)CN(C(=O)c2ccc(N3CCCCC3=O)cc2)C[C@@H]1c1ccc(Cl)cc1]

Amid coupling according to general procedure I:

Pyrrolidine intermediate: 5-Chloro-2-[(3RS,4RS)-4-(4-chloro-phenyl)-3-methyl-pyrrolidin-3-ylmethoxy]-pyridine (VII-1);

Carboxylic acid: 4-(2-Oxo-piperidin-1-yl)-benzoic acid (commercially available);

ES-MS m/e: 538.2 (M+Fl').

[$^3$H]SR142801 Competition Binding Assay hNK3 receptor binding experiment were performed using [$^3$H]SR142801 (Catalog No. TRK1035, specific activity: 74.0 Ci/mmol, Amersham, GE Healthcare UK limited, Buckinghamshire, UK) and membrane isolated from HEK293 cells transiently expressing recombinant human NK3 receptor. After thawing, the membrane homogenates were centrifuged at 48,000×g for 10 min at 4° C., the pellets were resuspended in the 50 mM Tris-HCl, 4 mM MnCl$_2$, 1 μM phosphoramidon, 0.1% BSA binding buffer at pH 7.4 to a final assay concentration of 5 μg protein/well. For inhibition experiments, membranes were incubated with [$^3$H]SR142801 at a concentration equal to K$_D$ value of radioligand and 10 concentrations of the inhibitory compound (0.0003-10 μM) (in a total reaction volume of 500 μl) for 75 min at room temperature (RT). At the end of the incubation, membranes were filtered onto unitfilter (96-well white microplate with bonded GF/C filter preincubated 1 h in 0.3% PEI+0.3% BSA, Packard BioScience, Meriden, Conn.) with a Filtermate 196 harvester (Packard BioScience) and washed 4 times with ice-cold 50 mM Tris-HCl, pH 7.4 buffer. Nonspecific binding was measured in the presence of 10 μM SB222200 for both radioligands. The radioactivity on the filter was counted (5 min) on a Packard Top-count microplate scintillation counter with quenching correction after addition of 45 μl of microscint 40 (Can berra Packard S. A., Zurich, Switzerland) and shaking for 1 h. Inhibition curves were fitted according to the Hill equation: $y=100/(1+(x/IC_{50})^{nH})$, where n$_H$=slope factor using Excel-fit 4 software (Microsoft). IC$_{50}$ values were derived from the inhibition curve and the affinity constant (K$_i$) values were calculated using the Cheng-Prussoff equation $K_i=IC_{50}/(1+[L]/K_D)$ where [L] is the concentration of radioligand and $K_D$ is its dissociation constant at the receptor, derived from the saturation isotherm. All experiments were performed in duplicate and the mean±standard error (SEM) of the individual $K_i$ values was calculated.

The results of compounds with a good hNK-3 receptor affinity are shown in the following table 1.

TABLE 1

| Example | Ki (uM) hNK3 |
|---|---|
| 1 | 0.0242 |
| 2 | 0.0478 |
| 3 | 0.0072 |
| 5 | 0.0618 |
| 6 | 0.0352 |
| 7 | 0.0043 |
| 8 | 0.0451 |
| 9 | 0.0563 |
| 10 | 0.0874 |
| 11 | 0.0106 |
| 12 | 0.0225 |
| 13 | 0.0087 |
| 14 | 0.015 |

| Example | Ki (nM) hNK3 |
|---|---|
| 15 | 0.015 |
| 16 | 0.0037 |
| 17 | 0.0023 |
| 18 | 0.0059 |
| 19 | 0.0112 |
| 20 | 0.0193 |
| 21 | 0.039 |
| 22 | 0.0272 |
| 24 | 0.0261 |
| 25 | 0.0044 |
| 26 | 0.0114 |
| 27 | 0.0931 |

The present invention also provides pharmaceutical compositions containing compounds of the invention, for example, compounds of formula I or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acid or its salts etc can be used as such excipients e.g. for tablets, dragées and hard gelatin capsules.

Suitable excipients for soft gelatin capsules are e.g. vegetable oils, waxes, fats, semi-solid and liquid polyols etc.

Suitable excipients for the manufacture of solutions and syrups are e.g. water, polyols, saccharose, invert sugar, glucose etc.

Suitable excipients for injection solutions are e.g. water, alcohols, polyols, glycerol, vegetable oils etc.

Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage at which compounds of the invention can be administered can vary within wide limits and will, of course, be fitted to the individual requirements in each particular case. In general, in the case of oral administration a daily dosage of about 10 to 1000 mg per person of a compound of formula I should be appropriate, although the above upper limit can also be exceeded when necessary.

Example A

Tablets of the following composition are manufactured in the usual manner:

|  | mg/tablet |
|---|---|
| Active substance | 5 |
| Lactose | 45 |
| Corn starch | 15 |
| Microcrystalline cellulose | 34 |
| Magnesium stearate | 1 |
| Tablet weight | 100 |

Example B

Capsules of the following composition are manufactured:

|  | mg/capsule |
|---|---|
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelantine capsules.

Example C

Suppositories of the following composition are manufactured:

|  | mg/supp. |
|---|---|
| Active substance | 15 |
| Suppository mass | 1285 |
| Total | 1300 |

The suppository mass is melted in a glass or steel vessel, mixed thoroughly and cooled to 45° C. Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

The following Examples illustrate the present invention without limiting it. All temperatures are given in degrees Celsius.

The invention claimed is:

1. A compound of formula I

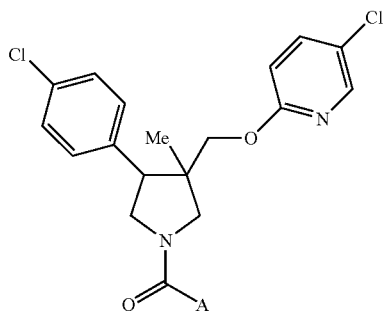

wherein
A is selected from the groups (a), (b) or (c):

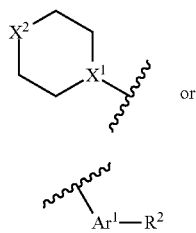

or is cycloalkyl, optionally substituted by lower alkyl (c);
Ar$^1$ is phenyl or a six membered heteroaryl;
X$^1$ is N or CH;
X$^2$ is N—R$^1$ or O;
R$^1$ is S(O)$_2$-lower alkyl, C(O)-cycloalkyl substituted by lower alkyl, or is C(O)-lower alkyl, lower alkyl, cyano, cycloalkyl or is a six membered heteroaryl substituted by lower alkyl, cyano, C(O)-lower alkyl, halogen, lower alkyl substituted by halogen or lower alkoxy; or is phenyl substituted by cyano or halogen; and
R$^2$ is lower alkyl, halogen, pyrazolyl, 3-methyl-[1,2,4]oxazolyl, 5-methyl-[1,2,4]oxadiazol-3-yl, pyridyl substituted by cyano, or is phenyl substituted by halogen, or is cyano, lower alkoxy, or is piperidin-2-one;
or pharmaceutically active salt, stereoisomer or a racemic or non-racemic mixture thereof.

2. The compound of claim 1, having formula IA

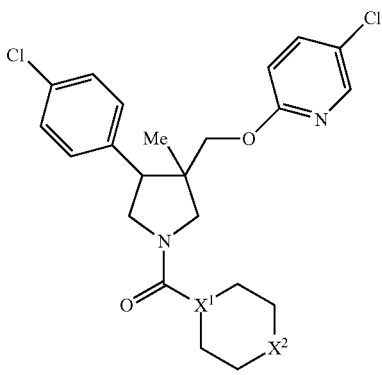

wherein
X$^1$ is N or CH;
X$^2$ is N—R$^1$ or O; and
R$^1$ is S(O)$_2$-lower alkyl, C(O)-cycloalkyl substituted by lower alkyl, or is C(O)-lower alkyl, lower alkyl, cyano, cycloalkyl or is a six membered heteroaryl substituted by lower alkyl, cyano, C(O)-lower alkyl, halogen, lower alkyl substituted by halogen or lower alkoxy; or is phenyl substituted by cyano or halogen;
or pharmaceutically active salt, stereoisomer or a racemic or non-racemic mixture thereof.

3. The compound of claim 2, selected from the group consisting of

[(3RS,4RS)-4-(4-chloro-phenyl)-3-(5-chloro-pyridin-2-yloxymethyl)-3-methyl-pyrrolidin-1-yl]-(4-methane sulfonyl-piperazin-1-yl)-methanone;

[(3RS,4RS)-4-(4-chloro-phenyl)-3-(5-chloro-pyridin-2-yloxymethyl)-3-methyl-pyrrolidin-1-yl]-[1-(1-methyl-cyclopropanecarbonyl)-piperidin-4-yl]-methanone;

[(3RS,4RS)-4-(4-chloro-phenyl)-3-(5-chloro-pyridin-2-yloxymethyl)-3-methyl-pyrrolidin-1-yl]-(tetrahydro-pyran-4-yl)-methanone;

1-{4-[(3RS,4RS)-4-(4-chloro-phenyl)-3-(5-chloro-pyridin-2-yloxymethyl)-3-methyl-pyrrolidine-1-carbonyl]-piperidin-1-yl}-ethanone;

[(3RS,4RS)-4-(4-chloro-phenyl)-3-(5-chloro-pyridin-2-yloxymethyl)-3-methyl-pyrrolidin-1-yl]-(1-isobutyl-piperidin-4-yl)-methanone;

1-{4-[(3RS,4RS)-4-(4-chloro-phenyl)-3-(5-chloro-pyridin-2-yloxymethyl)-3-methyl-pyrrolidine-1-carbonyl]-piperidin-1-yl}-2-methyl-propan-1-one;

[(3RS,4RS)-4-(4-chloro-phenyl)-3-(5-chloro-pyridin-2-yloxymethyl)-3-methyl-pyrrolidin-1-yl]-(1-cyclohexyl-piperidin-4-yl)-methanone; and

[(3RS,4RS)-4-(4-chloro-phenyl)-3-(5-chloro-pyridin-2-yloxymethyl)-3-methyl-pyrrolidin-1-yl]-(5'-methyl-3,4,5,6-tetrahydro-2H-[1,2']bipyridinyl-4-yl)-methanone.

4. The compound of claim 2, selected from the group consisting of

4-[(3RS,4RS)-4-(4-chloro-phenyl)-3-(5-chloro-pyridin-2-yloxymethyl)-3-methyl-pyrrolidine-1-carbonyl]-3,4,5,6-tetrahydro-2H-[1,2']bipyridinyl-5'-carbonitrile;

4-{4-[(3RS,4RS)-4-(4-chloro-phenyl)-3-(5-chloro-pyridin-2-yloxymethyl)-3-methyl-pyrrolidine-1-carbonyl]-piperidin-1-yl}-benzonitrile;

1-{4-[(3RS,4RS)-4-(4-chloro-phenyl)-3-(5-chloro-pyridin-2-yloxymethyl)-3-methyl-pyrrolidine-1-carbonyl]-3,4,5,6-tetrahydro-2H-[1,2']bipyridinyl-5'-yl}-ethanone;

[(3RS,4RS)-4-(4-chloro-phenyl)-3-(5-chloro-pyridin-2-yloxymethyl)-3-methyl-pyrrolidin-1-yl]-(5'-fluoro-3,4,5,6-tetrahydro-2H-[1,2']bipyridinyl-4-yl)-methanone;

[(3RS,4RS)-4-(4-chloro-phenyl)-3-(5-chloro-pyridin-2-yloxymethyl)-3-methyl-pyrrolidin-1-yl]-(5'-chloro-3,4,5,6-tetrahydro-2H-[1,2']bipyridinyl-4-yl)-methanone;

[(3RS,4RS)-4-(4-chloro-phenyl)-3-(5-chloro-pyridin-2-yloxymethyl)-3-methyl-pyrrolidin-1-yl]-(5'-trifluoromethyl-3,4,5,6-tetrahydro-2H-[1,2']bipyridinyl-4-yl)-methanone;

4-[(3RS,4RS)-4-(4-chloro-phenyl)-3-(5-chloro-pyridin-2-yloxymethyl)-3-methyl-pyrrolidine-1-carbonyl]-3,4,5,6-tetrahydro-2H-[1,3']bipyridinyl-6'-carbonitrile; and

[(3R,4R)-4-(4-chloro-phenyl)-3-(5-chloro-pyridin-2-yloxymethyl)-3-methyl-pyrrolidin-1-yl]-[1-(6-methoxy-pyridazin-3-yl)-piperidin-4-yl]-methanone.

5. The compound of claim 1, having formula IB

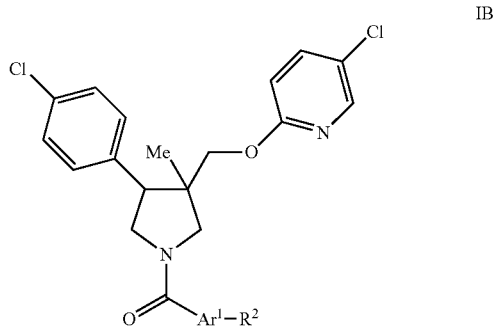

wherein

Ar¹ is phenyl or a six membered heteroaryl; and

R² is lower alkyl, halogen, pyrazolyl, 3-methyl-[1,2,4]oxazolyl, 5-methyl-[1,2,4]oxadiazol-3-yl, pyridyl substituted by cyano, or is phenyl substituted by halogen, or is cyano, lower alkoxy, or is piperidin-2-one;

or pharmaceutically active salt, stereoisomer or a racemic or non-racemic mixture thereof.

6. The compound of claim 5, selected from the group consisting of

[(3RS,4RS)-4-(4-chloro-phenyl)-3-(5-chloro-pyridin-2-yloxymethyl)-3-methyl-pyrrolidin-1-yl]-(6-methyl-pyridazin-4-yl)-methanone;

[(3RS,4RS)-4-(4-chloro-phenyl)-3-(5-chloro-pyridin-2-yloxymethyl)-3-methyl-pyrrolidin-1-yl]-(1-methyl-cyclopropyl)-methanone;

[(3RS,4RS)-4-(4-chloro-phenyl)-3-(5-chloro-pyridin-2-yloxymethyl)-3-methyl-pyrrolidin-1-yl]-(6-pyrazol-1-yl-pyridin-3-yl)-methanone;

[(3RS,4RS)-4-(4-chloro-phenyl)-3-(5-chloro-pyridin-2-yloxymethyl)-3-methyl-pyrrolidin-1-yl]-[4-(3-methyl-[1,2,4]oxadiazol-5-yl)-phenyl]-methanone;

4-[(3RS,4RS)-4-(4-chloro-phenyl)-3-(5-chloro-pyridin-2-yloxymethyl)-3-methyl-pyrrolidine-1-carbonyl]-benzonitrile;

[(3RS,4RS)-4-(4-chloro-phenyl)-3-(5-chloro-pyridin-2-yloxymethyl)-3-methyl-pyrrolidin-1-yl]-(6-methoxy-pyridin-3-yl)-methanone;

5-[(3RS,4RS)-4-(4-chloro-phenyl)-3-(5-chloro-pyridin-2-yloxymethyl)-3-methyl-pyrrolidine-1-carbonyl]-pyridine-2-carbonitrile;

[(3RS,4RS)-4-(4-chloro-phenyl)-3-(5-chloro-pyridin-2-yloxymethyl)-3-methyl-pyrrolidin-1-yl]-(4'-fluoro-biphenyl-4-yl)-methanone;

[(3RS,4RS)-4-(4-chloro-phenyl)-3-(5-chloro-pyridin-2-yloxymethyl)-3-methyl-pyrrolidin-1-yl]-[4-(5-methyl-[1,2,4]oxadiazol-3-yl)-phenyl]-methanone; and 1-{4-[(3RS,4RS)-4-(4-chloro-phenyl)-3-(5-chloro-pyridin-2-yloxymethyl)-3-methyl-pyrrolidine-1-carbonyl]-phenyl}-piperidin-2-one.

7. The compound of claim 1, wherein A is cycloalkyl, optionally substituted by lower alkyl.

8. A pharmaceutical composition comprising a therapeutically effective amount of a compound of formula I

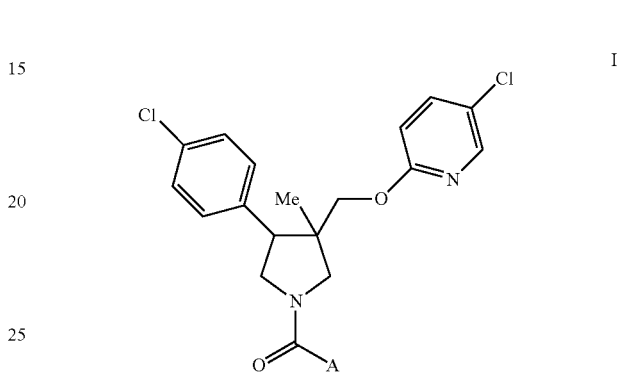

wherein

A is selected from the groups (a), (b) or (c):

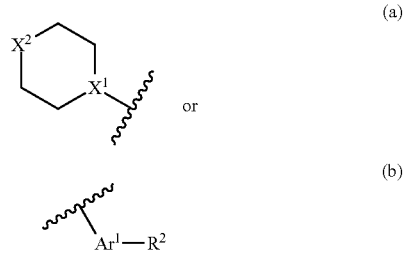

or is cycloalkyl, optionally substituted by lower alkyl (c);

Ar¹ is phenyl or a six membered heteroaryl;

X¹ is N or CH;

X² is N—R¹ or O;

R¹ is S(O)₂-lower alkyl, C(O)-cycloalkyl substituted by lower alkyl, or is C(O)-lower alkyl, lower alkyl, cyano, cycloalkyl or is a six membered heteroaryl substituted by lower alkyl, cyano, C(O)-lower alkyl, halogen, lower alkyl substituted by halogen or lower alkoxy; or is phenyl substituted by cyano or halogen; and R² is lower alkyl, halogen, pyrazolyl, 3-methyl-[1,2,4]oxazolyl, 5-methyl-[1,2,4]oxadiazol-3-yl, pyridyl substituted by cyano, or is phenyl substituted by halogen, or is cyano, lower alkoxy, or is piperidin-2-one;

or pharmaceutically active salt, stereoisomer or a racemic or non-racemic mixture thereof and a therapeutically acceptable carrier.

9. The composition of claim 8, wherein the compound of formula I has formula IA

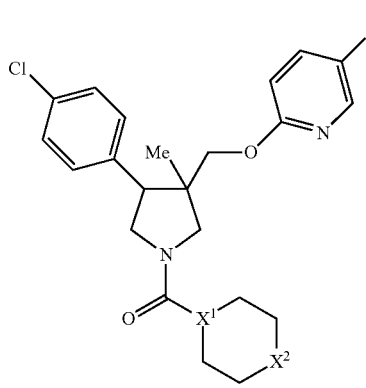

IA wherein
$X^1$ is N or CH;
$X^2$ is N—$R^1$ or O; and
$R^1$ is S(O)$_2$-lower alkyl, C(O)-cycloalkyl substituted by lower alkyl, or is C(O)-lower alkyl, lower alkyl, cyano, cycloalkyl or is a six membered heteroaryl substituted by lower alkyl, cyano, C(O)-lower alkyl, halogen, lower alkyl substituted by halogen or lower alkoxy; or is phenyl substituted by cyano or halogen;
or pharmaceutically active salt, stereoisomer or a racemic or non-racemic mixture thereof and a therapeutically acceptable carrier.

10. The composition of claim 8, wherein the compound of formula I has formula IB

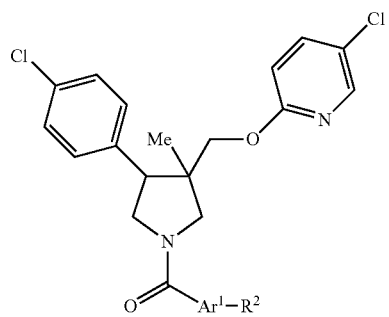

IB wherein $Ar^1$ is phenyl or a six membered heteroaryl; and $R^2$ is lower alkyl, halogen, pyrazolyl, 3-methyl-[1,2,4]oxazolyl, 5-methyl-[1,2,4]oxadiazol-3-yl, pyridyl substituted by cyano, or is phenyl substituted by halogen, or is cyano, lower alkoxy, or is piperidin-2-one;

or pharmaceutically active salt, stereoisomer or a racemic or non-racemic mixture thereof and a therapeutically acceptable carrier.

* * * * *